United States Patent [19]

Stephens

[11] 4,442,845

[45] Apr. 17, 1984

[54] PULSE CURVE ANALYSER

[76] Inventor: Frederick R. N. Stephens, 67 Coolawin Rd., Northbridge, N.S.W., 2063, Australia

[21] Appl. No.: 319,963

[22] Filed: Nov. 10, 1981

[51] Int. Cl.$^3$ ............................................... A61B 5/02
[52] U.S. Cl. ................................................... 128/687
[58] Field of Search .............................. 128/665–667, 128/687–694

[56] References Cited

U.S. PATENT DOCUMENTS

| 3,850,169 | 11/1974 | Geffen et al. | 128/687 |
| 4,013,067 | 3/1977 | Kressel et al. | 128/666 |
| 4,030,485 | 6/1977 | Warner | 128/667 |
| 4,338,950 | 7/1982 | Barlow, Jr. et al. | 128/687 |

FOREIGN PATENT DOCUMENTS 1340542 12/1973 United Kingdom .

OTHER PUBLICATIONS

Devi, V. et al., "A Processing System for Automatic On-Line Determination of LVET" *Changes in Health Core Instr. Due to uP Technology*, North-Holland Publ. Co. 1981 (from IFIP Conf: Rome (6–8 Feb. 1980) pp. 167–173.

Primary Examiner—Kyle L. Howell
Assistant Examiner—Francis J. Jaworski
Attorney, Agent, or Firm—Stevens, Davis, Miller & Mosher

[57] ABSTRACT

Disclosed is a pulse curve analyser for determining and displaying data on the rise time and/or fall time of an analog signal representing a transient cycle of a patient's body tissue pulsative blood color and/or density change waveform produced by physiological circulation activity.

4 Claims, 7 Drawing Figures

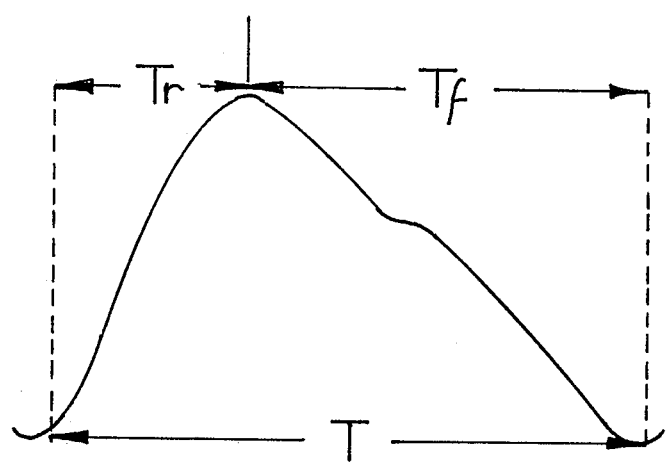
~FIG 1~

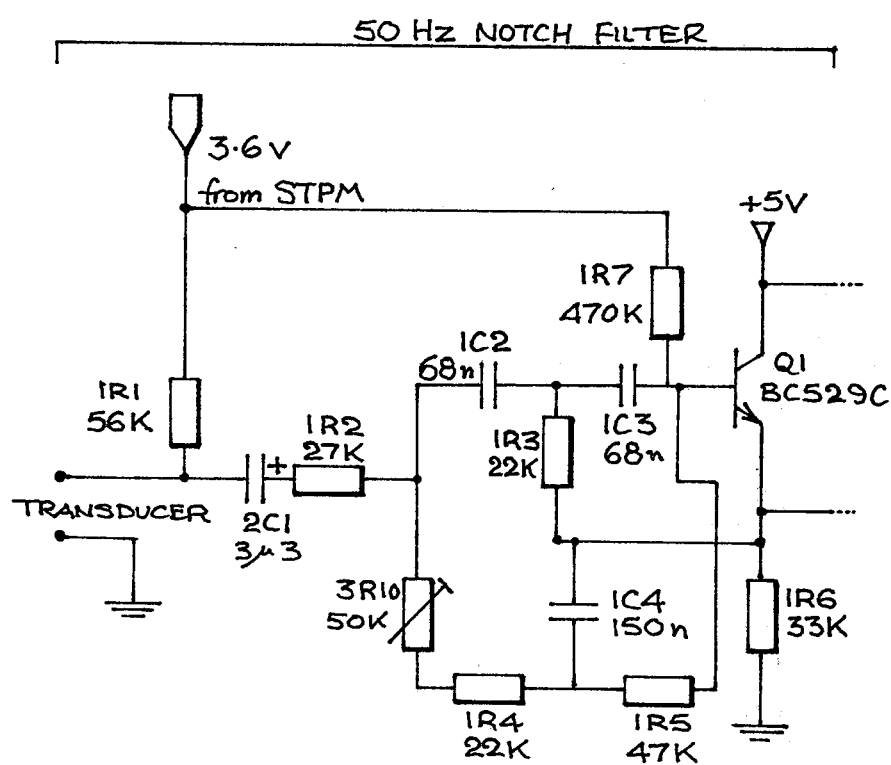
~ FIG 2 (LEFT) ~

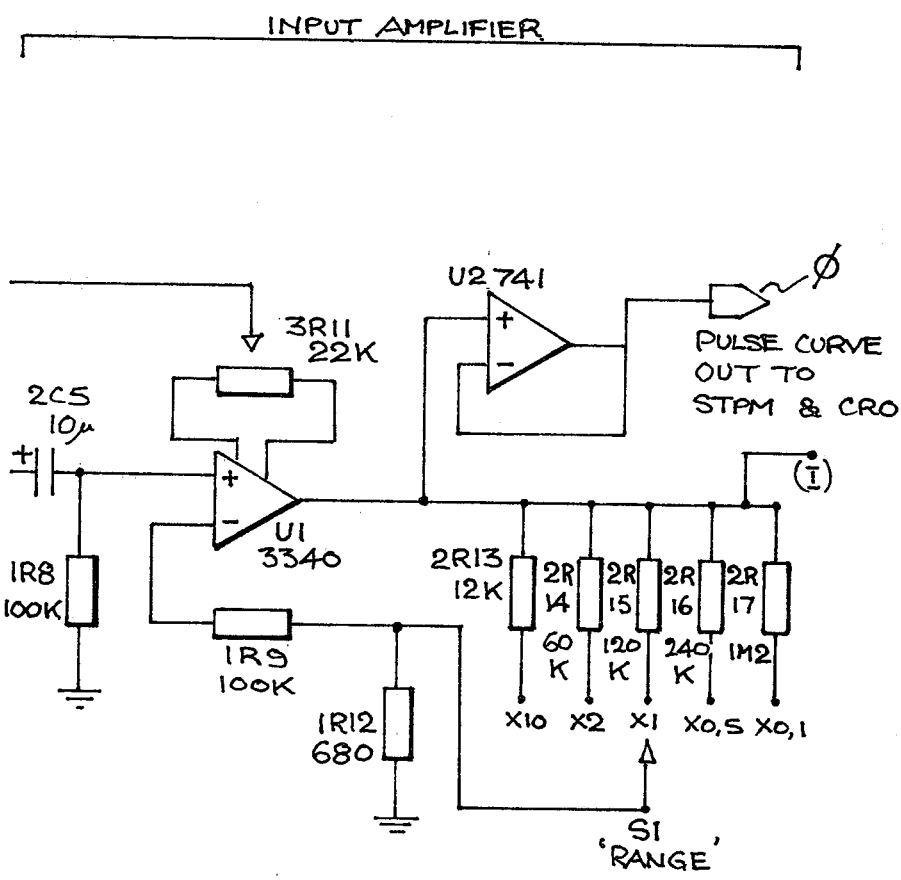
~FIG. 2 (RIGHT)~

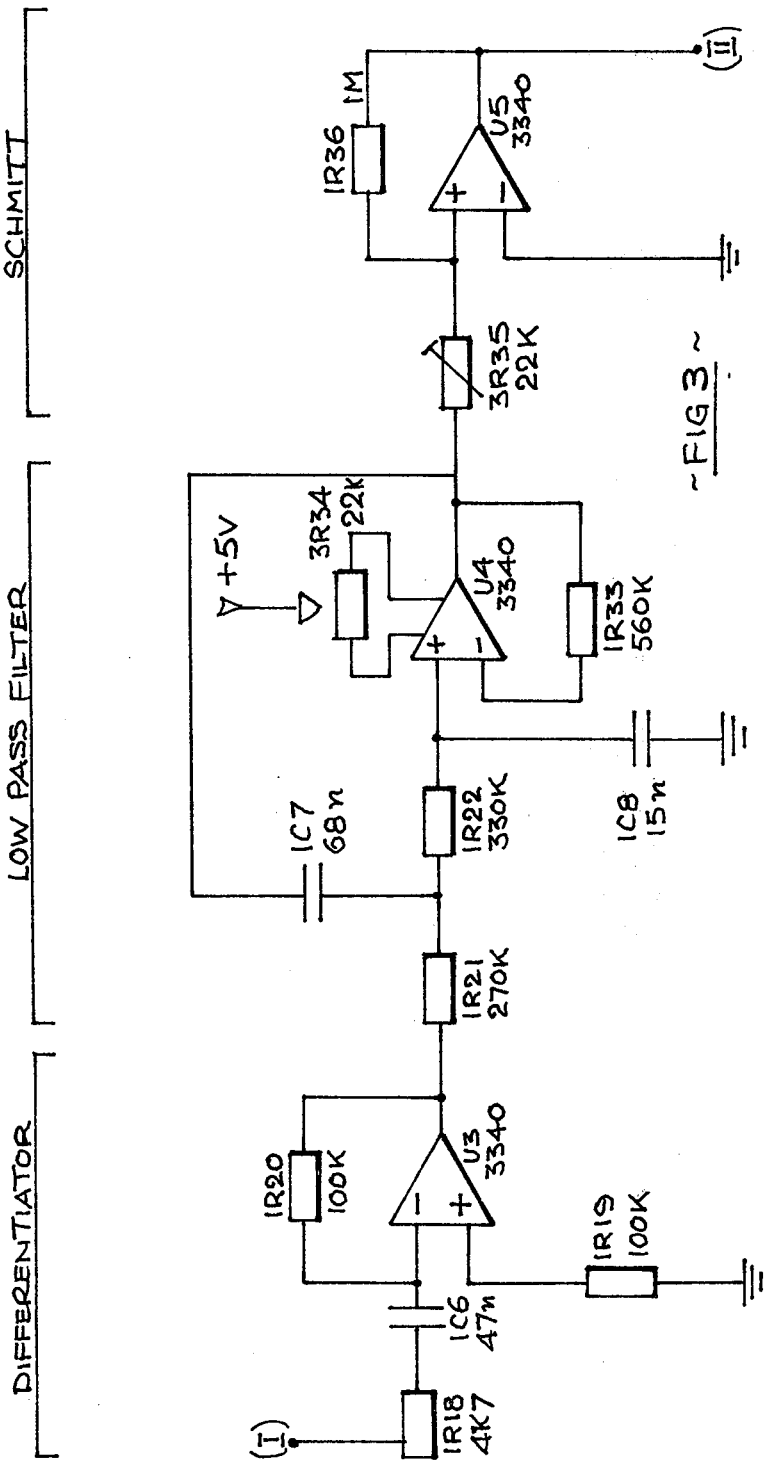

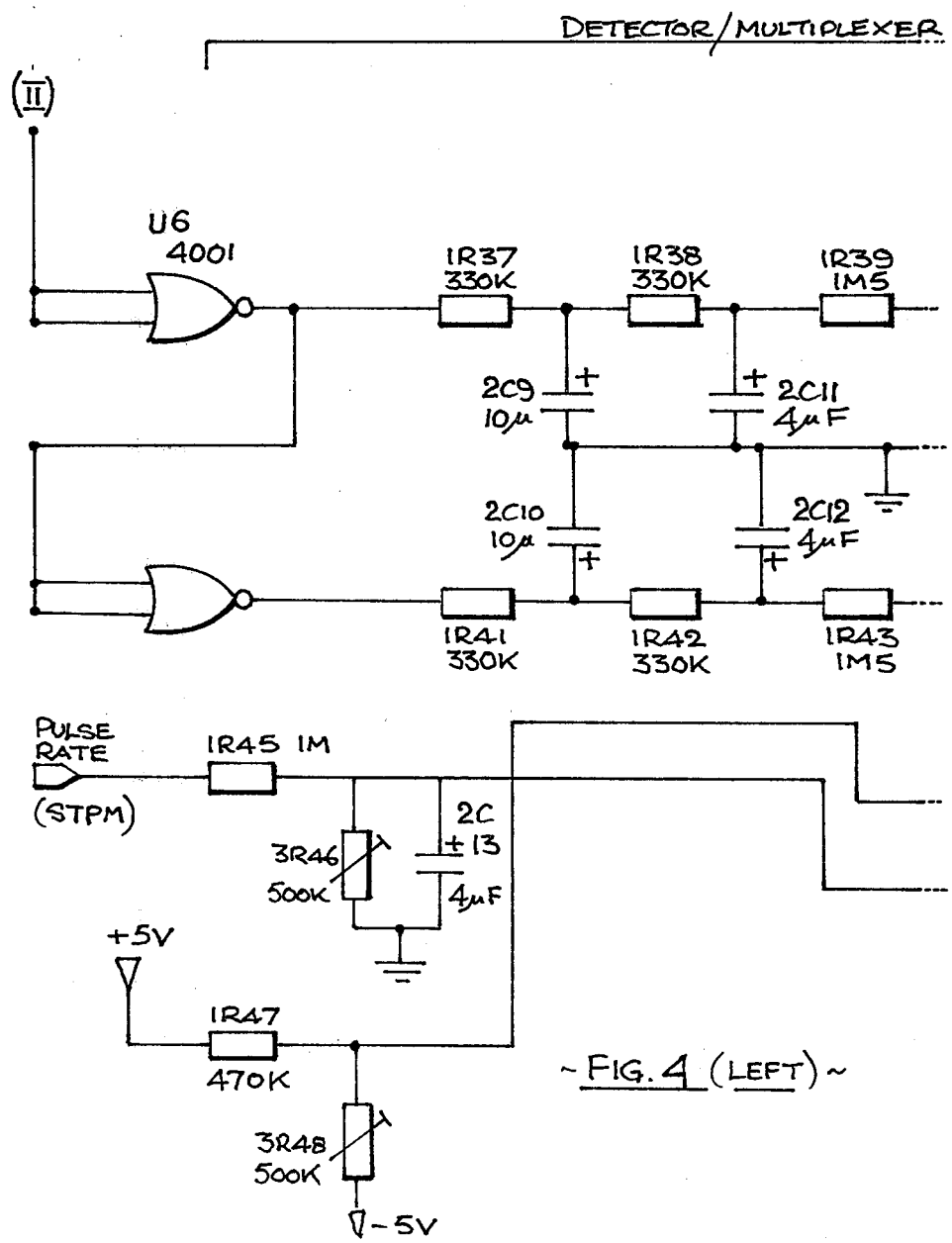
FIG. 4 (LEFT)

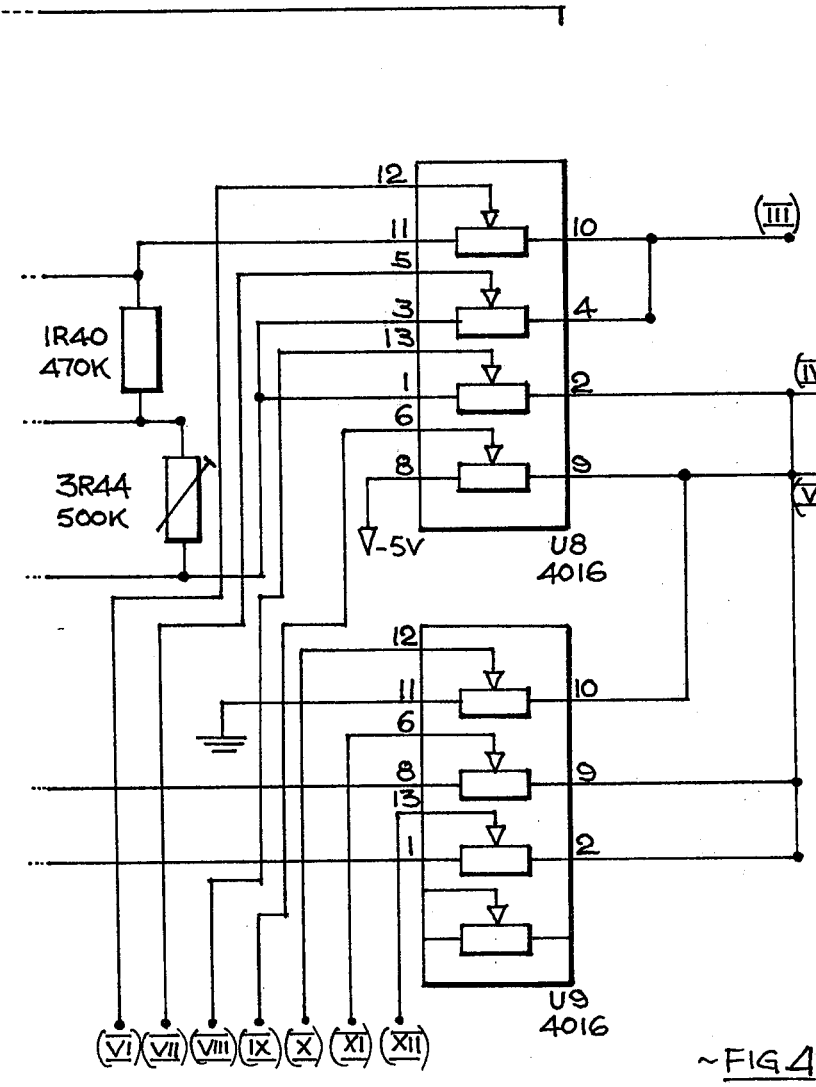
~FIG 4 (RIGHT)~

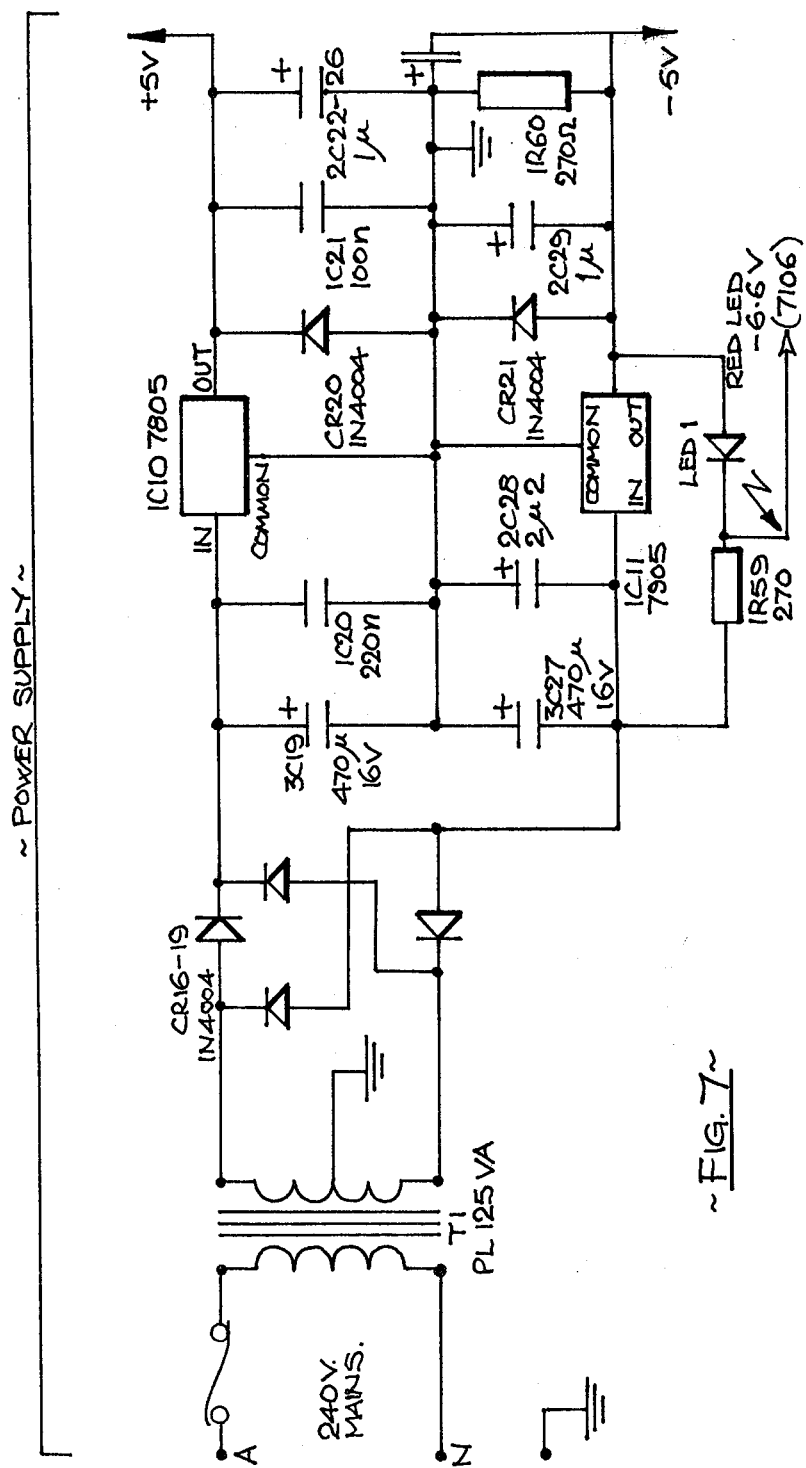
~FIG. 7~

PULSE CURVE ANALYSER

BACKGROUND OF THE INVENTION

1. Field of the Invention

This invention relates to electronic means for observing and/or measuring certain properties of the blood circulation in a living body.

2. Discussion of the Prior Art

Maintenance of life and viability of tissue cells depends on the physiological movement of blood in capillary circulation. The capillary circulation is contained by the small blood vessel network within which it is embraced between arterioles and venules. The capillary system is the interface between arterial and venous blood through all body tissue. The small vessel circulation is commonly referred to as the micro-circulation.

The blood volume is contained by the micro-circulation and the macro-circulation.

The macro-circulation includes the heart and blood vessels external to the micro-circulation. Traditional parameters of E.C.G., B.P. etc. are directed at the macrocirculation. Macrocirculatory parameters do not measure or reflect capillary activity or the effect of microcirculatory fluctuations.

The Stephens Tissue Perfusion Monitor or STPM (the subject of my Australian Pat. No. 465,302) samples and quantifies a signal from capillary circulation near skin surface to produce a measurement which is derived colorimetrically and non-invasively from micro-circulation in skin. The measurement, the Tissue Perfusion Index (TPI), is able to follow microcirculatory fluctuations and so provides indication of stability or change in activity of pulsatile micro-circulation at capillary level relative to an absolute reference level (say, 500 mV).

However, blood flow is a rhythmic activity capable of precise mathematical representation of curve shape in a sequence of analogue pulse curves. Despite the value of such a parameter as the TPI, the existing Tissue Perfusion Monitor is not intended to distinguish between differently shaped curves having the same area beneath them.

SUMMARY OF THE INVENTION

An object of the present invention therefore is to provide further information based on the shape of a pulse curve. Analogue pulse curve signals from either micro- or macro-circulatory sources can be monitored accordingly, and their differences measured and compared. It is known that various factors influence pulsatile micro-circulatory flow and in so doing alter the shape and/or amplitude of the curve. The measurement of these changes can add diagnostic information of value.

It is a further object of this invention to analyse and display parameters which relate to the shape of the pulse curve in terms of curve rise time "Tr" or curve fall time "Tf" and to the "rise/fall ratio" of the curve and to the rise and fall times, "Tr" and "Tf", relative to the pulse period "T".

It is yet another object of the invention to identify the positional presence of pressure wave effects such as the dichrotic notch in the basic curve cycle and to note significant inconsistencies and variations.

In one particular embodiment of the invention hereinafter described, continuous readouts are provided of the rise time "Tr" (m. sec.) and of the fall time "Tf" (m. sec.) and of the rise time of each pulse curve expressed in direct relation to the fall time, TR/TF, or of the rise or fall times expressed as a fraction of curve cycle period Tr/T or Tf/T. The data is correlated with the pulse rate to produce absolute parameters in milliseconds. In the case of the capillary the physiological mechanism involved in the analogue curve rise time is indicative of the time taken to "load" the capillary within the microcirculation, a normal adult human digital skin loading time usually approximating 0.2 secs. with considerable variation of the fall time which corresponds to the reductive phase of the cycle. The considerable variation in fall time relates mostly to change in pulse rate, but can sometimes be due to pathological disturbances.

According to the invention therefore, a pulse curve analyser comprises, in combination, light-responsive transducer means for sensing a patient's continuous physiological circulatory activity to produce a voltage waveform which is an analogue of said patient's body tissue pulsatile blood colour and/or density changes, means for processing said waveform to produce an output signal proportional to the time rate of change of the amplitude of said waveform, and means for displaying quantitatively and instantaneously the rise time and/or the fall time representative of a transient cycle of said waveform as a function of the period of said cycle.

BRIEF DESCRIPTION OF THE DRAWINGS

One particular embodiment of the invention defined in the preceding paragraph will now be described with reference to the accompanying drawings, in which:

FIG. 1 shows a mathematical representation of a pulse curve with its amplitude plotted against time, FIGS. 2 to 7 show the circuit of a pulse curve analyser wherein:

FIG. 2 includes notch filter and input amplifier circuits,

FIG. 3 includes a differentiator, a low pass filter and a Schmitt trigger,

FIGS. 4 and 6 include a detector/multiplexer,

FIG. 5 includes a digital display unit, and

FIG. 7 represents a power supply unit.

DETAILED DESCRIPTION OF A PREFERRED EMBODIMENT

Figure 5:
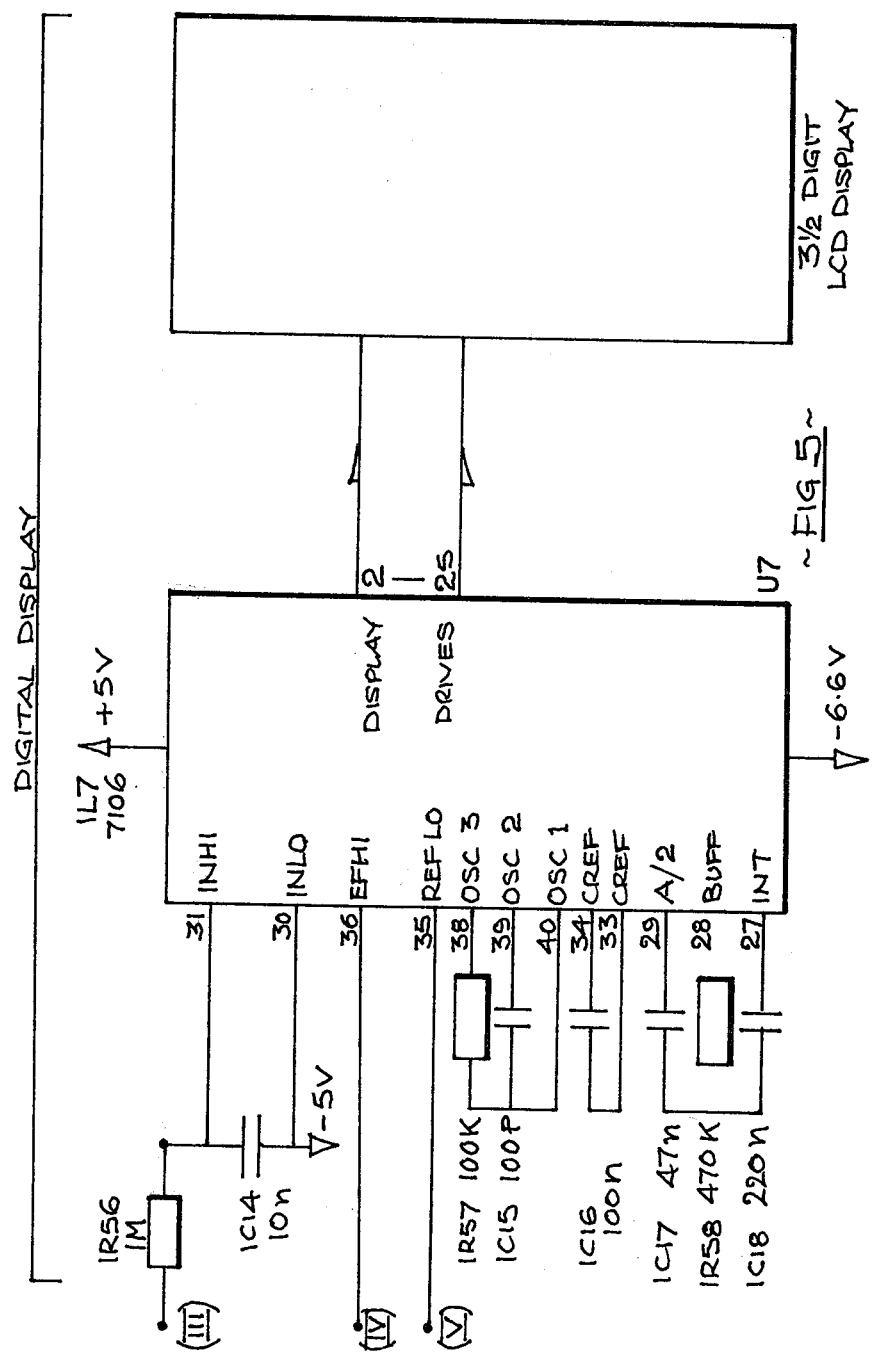

FIGS. 2 to 5 illustrate a tissue perfusion monitor with which the invention may be used. However, since this monitor does not per se form part of the invention, a detailed description thereof is not presented herein. Those of ordinary skill in the art, however, will readily perceive the structure and operation thereof from the detailed schematic drawings of FIGS. 2 to 5.

Figure 6:
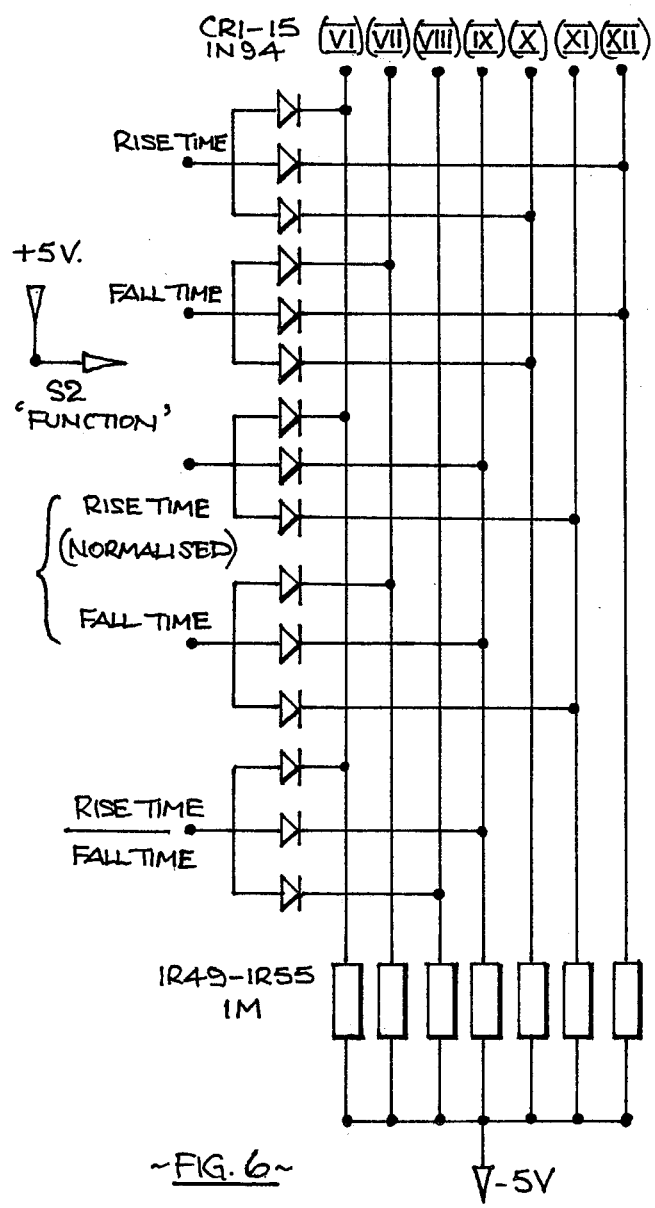

Upon referring to the drawings, particularly (FIGS. 6–11), it will be seen that a transducer is adapted to derive an electrical signal from a patient's body, for example, in a manner similar to that described in the specification of my Australian Pat. No. 465,302. Indeed, for convenience, this signal fed to the analogue curve analysis monitor may be taken from the pulse curve and pulse rate output terminals of the STPM. Circuitry for a tissue perfusion monitor is also shown in Australian patent application No. 75189/81 published Mar. 18, 1982.

Where a specified transducer such as above indicated is applied to the surface of mucous membrane or skin, a signal is derived as follows: Light from a light source within the transducer assembly becomes modulated by changes in activity of capillary blood circulation, and the so modulated light then falls on a detector which creates a wave form signal. The resulting waveform signal passes to the notch filter (FIG. 7), which is used to remove interference at power frequencies from induction or optical pick up. Said filter has a standard twin T circuit, tuned appropriately to, say, 50 Hz or 60 Hz.

3R10 is used to trim the filter to the centre frequency of any interference. The signal then passes to U1 which is an operational amplifier set up with adjustable gain over the range 25-65 dB. The output of this stage is buffered by U2 and passes to the host STPM to provide a CRO display, located either in the STPM or elsewhere.

The output of U1 also passes to U3 (FIG. 3) which acts to differentiate the pulse curve. Thus the output of U3 is proportional to the time rate of change of the input voltage thereto. U4 functions as a 2-pole low pass filter with linear phase. When properly offset (via R34) the output of U4 will be negative when the pulse curve voltage is rising, and positive when the pulse curve voltage is falling. The magnitude of this differential voltage is proportional to both the magnitude of the input voltage and its time rate of change.

The Schmitt trigger U5 will square up the output of U4, which then passes to the twin detector/filters consisting of U6, R37-44 and C9-12 (FIG. 4). The output of these two detectors is proportional to the fractional rise time (across R40) and the fractional fall time (across R44). These outputs are fractional to the pulse period, and are thus complementary.

The multiplexer consisting of U8 and U9 is used to apply the chosen set of inputs to U7 (FIG. 5), which is a true ratiometric voltmeter integrated circuit. The values of fractional rise and fall times are displayed by placing the output of the appropriate detector on the signal input of the digital voltmeter, with a standard voltage from R48 on the reference inputs.

Actual curve rise times and curve fall times in milliseconds are displayed by placing the appropriate detector output on the voltmeter signal input, and a voltage proportional to the pulse rate, obtained from the host STPM (via R45, R46) on the reference input.

Alternatively, if needed, the ratio of rise time to fall time can be displayed by placing the rise time detector output on the signal input, and the fall time detector on the reference input.

The calculated output is read numerically in this instance from an LCD readout driven by U7.

The product of "T" the pulse period and "Tr/T" can be displayed as an index in milliseconds of micro-circulatory loading time. Again, the product of "T" and "Tf/T" can be displayed as an index in milliseconds of the reductive phase Tf.

Indeed, the information may be presented in several different formats, viz:
(a) Rise time in milliseconds (Tr).
(b) Fall time in milliseconds (Tf).
(c) Rise time as a fraction of pulse period (Tr/T).
(d) Fall time as a fraction of pulse period (Tf/T).
(e) Rise time divided by fall time, as a fraction (Tr/Tf).

If desired, the readings for Tr/T and Tf/T or Tr/Tf may be selected by a multi-position switch, using the arrangement indicated in FIG. 10. Thus, with Tr/Tf (i.e. rise time to fall time ratio), when the rise time changes, a small increase in rise time in comparison with the relative reduction in the fall time discriminates change more sensitively than where the denominator is constant as in Tr/T or Tf/T.

The invention demonstrates that physiologically significant variations in rise time to fall time ratio readings do not necessarily correlate with TPI readings derived in common from a patient.

In conclusion therefore, it will be seen that a pulse curve analyser, constructed in accordance with the invention, provides information, from a pulse curve, which can be displayed in the form of precise measurements not available from a pulse monitor or even the sophisticated STPM. The CRO, although a convenient adjunct which may well be used to provide an auxiliary display of curve shapes, does not provide absolute measurements as does the pulse curve analyser, either in digital or analogue form as desired.

Thus, summarising, the pulse curve analyser is designed to extract information from a voltage waveform coming from a transducer, which may be optical, on the surface of skin or mucous membrane. In the case of activity of capillary blood circulation, information as to the phase of capillary blood loading and deoxygenation (reductive phase) appears in this voltage waveform. This waveform has a base frequency equivalent to the pulse, i.e. heart, rate of the patient.

The claims defining the invention are as follows:

1. A pulse curve analyser comprising, in combination, light-responsive transducer means for sensing a patient's continuous physiological circulatory activity by responding to light modulated by changes in capillary blood micro-circulation and producing a voltage waveform which is an analog of said patient's body tissue pulsatile blood color and/or density changes,
   means for processing said waveform to produce an output signal proportional to the time rate of change of the amplitude of said waveform, and
   means for displaying quantitatively and instantaneously data representing at least one of the rise time and the fall time of a transient cycle of said waveform as a function of the period of said cycle,
   said means for processing including a circuit wherein the output of said transducer means is fed to a notch filter, the output of which is fed to a operational amplifier whose output is buffered and then passed to a differentiator which in turn feeds a low pass filter having linear phase, the latter being offset whereby its output voltage is negative when said voltage waveform is rising, and positive when said voltage waveform is falling, and has a magnitude which is proportional to both the amplitude of said voltage waveform and its time rate of change.

2. A pulse curve analyser as claimed in claim 1, wherein the voltage output of said low pass filter is squared by a Schmitt trigger and then passed to twin detectors the respective outputs of which are proportional to the fractional rise time and fractional fall time of said voltage waveform with reference to a pulse cycle thereof, said last-mentioned outputs being applied by a multiplexer to chosen sets of inputs of a ratiometric voltmeter integrated circuit whereby the values of at least one of said rise and fall times are displayed.

3. A pulse curve analyser as claimed in claim 1, wherein data representing both the rise time and the fall time of a transient cycle of said waveform is displayed by said displaying means.

4. A pulse curve analyser as claimed in claim 1, wherein the values of both said rise and fall times are displayed.

* * * * *